United States Patent [19]

Kacian

[11] Patent Number: 5,364,763
[45] Date of Patent: Nov. 15, 1994

[54] TECHNIQUES FOR PREPARING SPECIMENS FOR BACTERIAL ASSAYS

[75] Inventor: Daniel L. Kacian, San Diego, Calif.

[73] Assignee: Gen-Probe Incorporated, San Diego, Calif.

[21] Appl. No.: 893,894

[22] Filed: Jun. 4, 1992

Related U.S. Application Data

[63] Continuation of Ser. No. 173,612, Mar. 25, 1988, abandoned, which is a continuation-in-part of Ser. No. 33,435, Apr. 1, 1987, abandoned.

[51] Int. Cl.$^5$ .................. C12Q 1/68; C12S 3/24; G01N 33/569
[52] U.S. Cl. .................. 435/7.32; 424/3; 435/4; 435/6; 435/7.1; 435/34; 435/268; 435/270; 435/810; 435/863; 435/961; 435/962; 435/975
[58] Field of Search .............. 435/4, 6, 7.1, 7.32, 435/34, 268, 270, 810, 863, 962, 975, 961; 436/175, 501, 825; 424/3

[56] References Cited

U.S. PATENT DOCUMENTS

| | | | |
|---|---|---|---|
| 3,502,779 | 3/1970 | Dye | 424/335 |
| 3,663,690 | 5/1972 | Eichel et al. | 424/94 |
| 4,358,535 | 11/1982 | Falkow et al. | 435/35 |
| 4,409,138 | 10/1983 | Maltz | 536/4.1 |
| 4,483,920 | 11/1984 | Gillespie et al. | 435/172.2 |
| 4,689,294 | 8/1987 | Boguslawski et al. | 435/6 |

FOREIGN PATENT DOCUMENTS

0045285 2/1982 European Pat. Off. .
0079139 5/1983 European Pat. Off. .

OTHER PUBLICATIONS

Lieberman, J., *Measurement of Sputum Viscosity in a Cone-Plate Viscometer. II. An Evaluation of Mucolytic Agents in Vitro*. American Review of Respiratory Disease 97:662-672 (1968).
Webb, W. R., *Clinical Evaluation of a New Mucolytic Agents, Acetyl-Cysteine*. Journal of Thoracic and Cardiovascular Surgery 44:330-343 (1962).
Mackay, M., Hilgartner, C. A., and Dounce, A. L., *Further Studies of DNA-Nucleoprotein Gels and Residual Protein of Isolated Cell Nuclei*. Experimental Cell Research 49:533-557 (1968).
Sherry, S., Tillet, W. S., and Christensen, L. R., *Presence and Significance of Desoxyribose Nucleoprotein in the Purulent Pleural Exudates of Patients*. Proc. Soc. Exp. Biol. Med. 68: 179-184 (1948).
Tillet, W. S., Sherry, S., and Christensen, L. R., *Streptococcal Desoxyribonuclease: Significance in Lysis of Purulent Exudates and Production by Strains of Hemolytic Streptococci*. Proc. Soc. Exp. biol. Med. 68: 184-188 (1948).
Lieberman, J. and Kurnick, N. B., *Influence of Deoxyribonucleic Acid Content on the Proteolysis of Sputum and Pus*. Nature (No. 4859): 988-990 (1962).
Armstrong, J. B., and White, J. C., *Liquefaction of Viscous Purulent Exudates by Deoxyribonuclease*. Lancet p. 739 (Dec. 9, 1950).
Bornstein, A. A., Chen, T.-M., and Dulfano, M. J., *Disulfide Bonds and Sputum Viscoelasticity*. Biorheology 15:261-267 (1978).
Puchelle, E., Zahm, J. M., and Havez, R., *Biochemical and Rheological Data in Sputum. III-Relationship between the Biochemical Constituents and the Rheological Properties of Sputum*. Bull. Physio-Path. Resp. 9: 237-256 (1973) [In French, English abstract cited].
Rawlins, G. A., *Liquification of Sputum for Bacteriological Examination*. Lancet p. 539 (Sep. 12, 1953).
Lightowler, J. E. and Lightowler, N. M., *Comparative Mucolytic Studies on Dithiothreitol, N-Acetyl-cysteine*
(List continued on next page.)

*Primary Examiner*—David Saunders
*Attorney, Agent, or Firm*—Lyon & Lyon

[57] ABSTRACT

Methods and compositions for improved liquification of mucoid secretion specimens by treatment with a disulfide bond reducing agent and a DNA digestion agent, and for improved concentration of selected bacterial species from such specimens, are disclosed. The disclosure has applicability to bacterial assay techniques including nucleic acid hybridization, culture and stain techniques.

44 Claims, No Drawings

OTHER PUBLICATIONS

*and L-Cysteine on Human Respiratory Mucus In Vitro and Their Effects on the Rate of Flow of Mucus in the Exposed Trachea of the Rat on Topical Application.* Arch. Int. Pharmacodyn. 189. 53–58 (1971).

Sherry, S. and Goeller, J. P., *The Extent of the Enzymatic Degradation of Desoxyribonucleic Acid (DNA) in Purulent Exudates by Streptodornase.* (1950).

Tillett, W. S. and Sherry, S., *The Effect in Patients of Streptococcal Fibrinolysin (Streptokinas) and Streptococcal Desoxyribonuclease on Fibrinous, Purulent, and Sanguinous Pleural Exudations.* (1948).

Sherry, S. Johnson, A., and Tillett, W. S., *The Action of Streptococcal Desoxyribose Nuclease (Streptodornase), In Vitro and on Purulent Pleural Exudations of Patients.* (1949).

Kent, Patricia T., and Kubica, George P., *Public Health Mycobacteriology; A Guide For The Level III Laboratory.* U.S. Department of Health and Human Services, (1985).

Sommers et al, in Lennette et al (Eds.) *Manual of Clinical Microbiology,* 4th Edition, American Society for Microbiology, Washington, D.C., 1985, pp. 226–229.

Price, P. A., et al., J. Biol. Chem., 244(4):929–932 (1969).

Junowicz, E., et al., Biochim. et Biophys. Acta, 312:72–84 (1973).

Tullis, R. H., et al., Anal. Biochem. 107:26–264 (1980).

Fleisher, et al., Inorg. Chem. 25:3549–3551 (1986).

Hertzberg & Dervan, Biochemistry, 23:3934–3945 (1984).

Amer. Rev. Resp. Disease 97:662–672, 1968 (Lieberman).

Mack & Dervan, J. Am. Chem. Soc. 112:4604–4607 (1990).

Chemical Abstracts 85(23):173830d, 1976 (Martinetti).

Chemical Abstracts 84(19):130190g, 1976 (McNiff, et al.).

Nicolaou, et al., Angew. Chem. Inte. Ed. Engl. 28:1272–1275 (1989).

Sheffner, Ann. N.Y. Acad. Sci., 106:298–310 (1963).

Sigman, Acc. Chem. Res. 19:180–186 (1986).

Sluka, et al., Science 238:1129–1132 (1987).

Taylor, et al., Tetrahedron 40:457–465 (1984).

*The Pharmacological Basis of Therapeutics* (Goodman & Gilman, eds.), "Mucolytics", pp. 955–956 (5th ed. 1975).

*Worthinghton Enzyme Manual,* Worthington Biochemical Corporation, Freehold, N.J., 1972, p. 85.

TECHNIQUES FOR PREPARING SPECIMENS FOR BACTERIAL ASSAYS

BACKGROUND OF THE INVENTION

A. Related Applications

This application is a continuation of U.S. application Ser. No. 07/173,612, filed Mar. 25, 1988 and now abandoned, which is a continuation-in-part of U.S. application Ser. No. 07/033435, filed Apr. 1, 1987 and now abandoned.

B. Field of the Invention and Related Art

Investigators in the 1950's to early 1960's recognized that there were differences in the composition of various mucoid secretions including sputa depending upon source and the nature of a given disease process. In particular, the existence of sputa that were classified as mucoid and lacked inflammatory cells such as are commonly found in association with infectious processes, as well as sputa containing such cells (classified as purulent), was appreciated. It was suggested that both protein components and DNA were likely to contribute to sputum viscosity, and evidence in support of this was collected. In particular, DNAses and proteases were shown to have the ability to liquify sputa and pus to some extent. DNAses appeared to have more activity when used with purulent sputa; whereas, proteases were more effective with mucoid sputa. Lieberman, *Amer. Rev. Resp. Disease*, Vol. 97, pp. 662–672 (1968).

In addition to enzymes, a variety of other agents such as detergents, salts, oxidizing and reducing agents, etc. were tried as liquifying agents, and a number worked more or less successfully. Virtually all had some disadvantages for one or more of the usual purposes, which included liquification for use in laboratory test procedures and for therapy in patients.

In the early 1960's, the use of the sulfhydryl reagent N-acetyl-L-cysteine was reported effective for liquifying mucoid secretions, both purulent and mucoid in nature. Webb, *J. Thoracic & Cardiovascular Surg.*, Vol. 44, pp. 330–343 (1962). It was claimed that the reagent was capable of liquifying both mucous (the protein component thought to be responsible for most of the viscosity in mucoid specimens) and DNA, which had been postulated to be a significant contributor to viscosity in purulent specimens. This reagent and the related compound, dithiothreitol (U.S. Pat. No. 3,502,779 (Mar. 24, 1970)), gave superior liquification of many mucoid specimens for a variety of purposes, as Judged by comparison with previous procedures. Although sulfhydryl reagents may play a role in helping to disrupt DNA-protein complexes (nucleoprotein gels), they do not affect the viscosity of pure DNA solutions (which may be very viscous), and it is likely that some of these early investigators were observing the effects of DNAse and protease contamination of their preparations. The inhibitory effect of DNA upon proteases was recognized by some of the earliest investigators. Thus, claims were made that suggested that sulfhydryl reagents alone could handle both protein and DNA contributions to viscosity that may have deterred others from investigating the usefulness of a combination of sulfhydryl reagents and DNAse.

In more recent work in which attempts were made to be more quantitative in measuring sputum theological properties than in the earlier studies, investigators have generally discounted the effect of DNA on sputum viscosity. They have found no correlation between DNA content and viscosity; however, they do not appear fully to appreciate that the viscosity contributed by the DNA will depend upon its physical state as well as amount. Large, double-stranded DNA will yield a significantly more viscous solution than will short or single-stranded fragments.

Thus, in spite of an early appreciation that individual mucoid secretions had variable properties and that these variations might be related to differences in the relative amounts of mucous glycoprotein and DNA present, no investigators have reported trying sulfhydryl reagents and DNAse in combination for the liquification of mucoid specimens.

Methods and compositions used to liquify sputum and other mucoid or viscous biological specimens in a bacterial assay context have suffered from various drawbacks. Dilute NaOH will liquify sputum, but is less efficient than dithiothreitol (DTT) and in addition, kills many bacteria and destroys bacterial RNA. (Such RNA is therefore not available for performing nucleic acid hybridization assays.) Metal chelators such as EDTA have been used without major success. Ascorbic acid/copper sulfate/sodium percarbonate mixtures are less effective than DTT and also hazardous to use. Detergents such as sodium dodecyl sulfate are toxic to many bacteria, less effective than DTT, and interfere with stain techniques. Sodium hypochlorite also interferes with stain techniques, kills many bacteria and is somewhat unpleasant to work with.

In addition to questions relating to the liquification of sputum and other mucoid or viscous specimens, the isolation or concentration of bacterial species from such specimens has been problematic in certain cases. In particular, bacteria of the genus Mycobacterium are difficult to separate in satisfactory quantities from sputum specimens because their density is close to that of water, which renders centrifugation inefficient.

The organisms of the genus *Mycobacterium* are responsible for significant mortality and morbidity in humans. *M. tuberculosis* is the most clinically significant mycobacterial pathogen. In 1983, an estimated 50,000 Americans had tuberculosis, with 23,846 cases being reported. TB Statistics: States and Cities, *Morbidity and Mortality Weekly Report*, Vol. 33, p. 62 (1983). Worldwide, tuberculosis is responsible for approximately three million deaths annually. Youmans, G. P., *Tuberculosis*, pp. 107, W. B. Saunders (Philadelphia: 1979). The second most clinically significant group of mycobacteria is the *M. avium* complex, which is composed of *M. avium* and *M. intracellulare*. Good & Snider, *J. Infect. Dis.*, Vol 146, pp. 829–833 (1982).

Traditional methods for the detection, isolation and identification of Mycobacterium species include the acid-fast staining procedures, culture techniques and biochemical confirmatory procedures. The potential presence of mycobacteria is determined through microscopic examination of a specimen that has been treated with an appropriate stain. The presence of acid-fast bacilli is indicative of the presence of mycobacteria. After the initial detection of mycobacteria, the specimen may be further processed and cultured. The two most commonly used culture media are the Lowenstein-Jensen media and the Middlebrook media. After growth is attained, further differential tests may be applied to identify the mycobacterial species present. The Center for Disease Control has recommended a series of 18 tests that allow for specific identification of nearly 90 percent of mycobacterial species. Kubica, G. P., in *The Mycobacteria: A Sourcebook*, Part A (Kubica & Wayne, eds.), pp. 133-175, Marcel Dekkar (New York: 1984).

Techniques used to concentrate mycobacteria from sputum have also included, first, treatment with DTT (to liquify) and NaOH (to kill off non-mycobacteria and to release mycobacteria from associated white blood cells), followed by centrifuging for about 15 minutes at 3800×g and neutralization of the solution. Recovery of pelleted mycobacteria is inefficient, and this method is not ideally adapted to a sensitive assay procedure because recovery is not quantitative. Furthermore, the NaOH reagent used can kill the mycobacteria if left unneutralized too long in the specimen. Other concentration techniques including chloroform extraction, flocculation, flotation centrifugation and entrapment in aluminum hydroxide or magnesium hydroxide gels have proven largely ineffective or problematic, and are not widely used today. (See review in Willis, H. S., and Cummings, M. M., Diagnostic and Experimental Methods in Tuberculosis (1952) Springfield: C. C. Thomas.) High speed ultracentrifugation, although slightly better in concentrating mycobacteria than routine centrifugation, is expensive and does not yield a quantitative recovery.

SUMMARY OF THE INVENTION

The present invention is directed to: (1) liquification of mucoid secretion and other viscous biological specimens and; (2) concentration of bacterial species such as mycobacteria, in particular in the context of assays for detecting the presence or absence of selected bacterial species in biological specimens.

Accordingly, a first aspect of the invention is directed to improved methods and compositions for liquifying mucoid secretion and other viscous biological specimens, utilizing a liquifying combination comprising a disulfide bond reducing agent and a DNA digestion agent.

A second aspect of the invention is directed to concentrating a bacterial species from a biological specimen (including but not limited to viscous biological specimens such as mucoid secretion specimens). According to this aspect of the invention, a method and means are provided whereby bacteria associated with white blood cells in a biological specimen are concentrated by direct separation (e.g. by centrifugation) of the intact white blood cells, and then the white blood cells are selectively lysed such that the bacteria of interest remain substantially cellularly intact.

The methods and compositions disclosed herein will be seen to be applicable to a wide range of bacterial assay techniques, including nucleic acid hybridization, culture and stain techniques.

DETAILED DESCRIPTION

The present invention relates to improved methods and compositions useful in assaying mucoid secretion specimens or other biological specimens for the presence of selected bacterial species. In particular, the invention discloses improved means for determining whether a mucoid secretion specimen of, for example, sputum, cervical mucous, bronchial mucous, vaginal mucous or other mucous taken from a human or other animal is infected with a given bacterial species. The invention can also be applied to other biological samples or specimens such as urine, cerebral spinal fluid, whole blood, or other body fluids and secretions.

The invention addresses a number of problems that have heretofore existed in performing such assays. First, the invention provides improved means for achieving liquification of mucosal secretion samples, such as sputum, and other viscous biological samples. Such liquification is necessary in order to obtain samples that can be effectively and accurately assayed for selected bacterial species. According to this aspect of the invention, a liquifying combination is used comprising a disulfide bond reducing agent and a DNA digestion agent. A preferred reducing agent is dithiothreitol, while a preferred DNA digestion agent is deoxyribonuclease I purified from bovine pancreas. These components are representative of reagents which are extraordinarily good, in combination, in liquifying mucoid secretion specimens and are likewise compatible with other requirements of a successful assay for selected bacterial species in such specimens. Although a number of liquification methods have been used in the past, none is believed to be as effective as the method disclosed herein.

Secondly, the invention relates to improved methods for concentrating selected bacterial species from mucosal secretion specimens or other biological specimens for the purposes of assaying for the presence of such species. In particular, the prior art has had considerable difficulty in concentrating or isolating such bacteria as those in the genus Mycobacterium because these bacteria, in conventional specimen processing media, do not lend themselves to separation using conventional techniques such as centrifugation. According to this aspect of the invention, white blood cells associated with bacteria are concentrated, preferably by centrifugation, and then are selectively lysed such that the bacteria remain substantially cellularly intact. The concentrated bacteria, for example mycobacteria, may then be assayed in the concentrated specimen using methods and compositions disclosed herein.

The methods and compositions disclosed herein are suitable for use in a number of bacterial assay systems, including acid-fast staining procedures, culture techniques, biochemical confirmatory procedures and, particularly, nucleic acid hybridization techniques. The invention is particularly suited for assaying for the presence of Mycobacterium in sputum samples.

Nucleic acid hybridization techniques are preferably used in the present invention to identify mycobacteria directly from sputum or other mucoid secretion specimens within three hours of specimen processing. Nucleic acid hybridization assays are based on the ability of complementary nucleic acid strands to come together to form double-stranded complexes. See generally Minson & Darby, "Hybridization Techniques" in New Developments in Practical Virology, pp. 185-229, Alan R. Liss, Inc. (New York: 1982. Such assays are available from Gen-Probe, Inc. (San Diego, California). They may use, for example an $^{125}$I-labeled single-stranded DNA probe complementary to the ribosomal RNA of the target organism (Kohne, et al., *in Legionella: Proceedings of the 2nd International Symposium* (Thornsberry, et al., eds.), pp. 107-108, American Society for Microbiology (Washington: 1984)). After the ribosomal RNA is released from the organism using a lysing technique, the $^{125}$I-DNA probe combines with the target organism's ribosomal RNA to form a stable DNA:RNA hybrid. The remaining labeled, non-hybridized probe is separated from the hybridized DNA probe using a solid phase separation suspension. The absorbed labeled DNA:RNA hybrids are counted in a gamma counter and test results calculated as the ratio of the counts in the patient specimen to the counts of a negative control.

Each of the assay techniques discussed above utilizes a liquification step in order to render the starting sputum or other mucoid secretion specimen, or other viscous biological specimen, less viscous. The viscosity of sputum is attributable in part to the presence of mucus glycoproteins. In addition, purulent (infected) sputum or other biological samples may contain large amounts of viscous DNA generated as a result of host defensive responses from destroyed bacteria (e.g., mycobacteria) and from dead white blood cells (primarily macrophages and granulocytes).

The present invention utilizes a mixture of a disulfide (cysteine) bond reducing agent and a DNA digestion agent such as a DNAse to achieve liquification of a starting sputum sample or other viscous or mucoid biological sample. These agents should be chosen and applied such that the extent of disulfide bond and phosphodiester bond cleavage attributable to the agents is sufficient to effect, in combination, a satisfactory level of liquification. In particular, a highly preferred disulfide bond reducing agent is dithiothreitol (DTT), while a highly preferred DNA digestion agent is deoxyribonuclease I (DNAse I) purified from bovine pancreas. Other useful disulfide bond reducing agents may include N-acetyl-cysteine, cysteine and 2-mercaptoethane sulfonate. Endonucleases are generally preferred as more efficient liquification agents than exonucleases.

It has been discovered that the combination of such materials yields liquification results which surpass methods or compositions heretofore practiced or known to the art. These materials appear to work in combination in that the DTT reducing agent, for example, cleaves disulfide bonds which bridge proteinaceous chains in the mucus glycoproteins, while the DNAse I enzyme, for example, cleaves DNA molecules present in the purulent sputum specimen.

A starting specimen of sputum or other mucoid secretion may be liquified by either sequential or simultaneous exposure to the reducing and DNA digestion agents discussed above. In a representative technique, 1 ml of a 0.01 M solution of DTT in 0.9% sterile saline is added to an equal volume of sputum specimen. The sample is then vortexed until it liquifies (less than one minute typically). The sample is then incubated for 5 minutes at room temperature (18°-25° C.) and once again vortexed briefly. The solubilized sputum (2 ml) is then combined with about 1 ml of an approximately 0.1 M solution of DTT in 0.9% sterile saline in a 50 ml conical centrifuge tube. To this mixture is then added 4 drops (about 190 microliters) of DNAse I (purified from bovine pancreas; Sigma Chemical Co. or Cooper Biomedicals, approx. 1000–2000 Kunitz units/mg) at a concentration of approximately 7500 Kunitz units/ml in 0.85% (w/v) NaCl, 5 mM $MgCl_2$, 5 mM $CaCl_2$ (0.02% sodium azide preservative). The mixture is vortexed briefly and incubated for 5 minutes at room temperature. About 30 ml of 0.9% sterile saline is then added to the centrifuge cone with mixing, and the sample is centrifuged at 1900–2100×g for 5 minutes in a swinging bucket rotor.

The DNAse solution preferably contains a source of magnesium ($Mg^{2+}$) and calcium ($Ca^{2+}$) which serves to activate the enzymatic activity of the DNAse, stabilize the enzyme during storage ($Ca^{2+}$) and stabilize the cell wall of the white blood cells in the sputum sample during centrifugation. One important aspect of the present invention is the discovery that the ability to concentrate (i.e., separate or isolate) mycobacteria from sputum specimens into a concentrated specimen is greatly enhanced if the white blood cells (primarily macrophages in the case of mucosal sputum) in the specimen are kept cellularly intact during the concentration of the bacteria. This result appears to be due to the fact that such white blood cells, during the immune response, associate to a high degree with the target bacteria, as for example mycobacteria. Such association may be in the nature of incorporation of the bacteria into the interior of the white blood cells, or in the nature of surface adherence of the cells to the bacteria. The present invention utilizes this association to improve the ability to concentrate and isolate the target bacteria by use of a conventional centrifuge step at readily attainable spin rates.

In view of this significant discovery, it is clear that any composition used to liquify the starting sputum specimen must be chosen so as to allow rapid and complete digestion of the mucus glycoprotein and DNA components and at the same time not substantially degrade the cellular integrity of the white blood cells resident in the specimen. The desirability of a component such as $Mg^{2+}$ or $Ca^{2+}$ which aids digestion (liquification) of the sputum or other mucoid secretion specimen while simultaneously promoting white blood cell stability is also apparent.

It will be further appreciated from the following discussion that the use of a carefully chosen combination of specimen digesting agents such as that disclosed herein will be highly advantageous to the overall scheme of a successful assay. In particular, the use of a DNAse or other nuclease in the context of a nucleic acid hybridization type assay would be considered disadvantageous under normal circumstances given the fact that such enzymes would digest the hybridization probe and/or bacterial target nucleic acids used later in the assay. However, the present invention circumvents this problem and is able to use a DNAse digestion agent to great advantage by utilizing a class of DNAse that can be specifically inactivated during later processing stages. Equally importantly, however, is the fact that the DNAses to be used herein will retain their activity even in the presence of other agents, such as cell lysing agents, that are also used in the practice of the present invention. It is seen, therefore, that the combinations of liquification agents (for specimen digestion) that are claimed herein, in addition to achieving remarkably good liquification results, are carefully suited to the practice of the overall assay invention. DNAse I purified from bovine pancreas is one example of a DNA digestion agent capable of retaining its activity in the presence of a cell lysing reagent ( in particular sodium deoxycholate) , and this DNA digestion agent is therefore preferred in the practice of the present invention.

The functional requirements attaching to liquification agents appropriate for use in the present invention are related to process steps which follow the liquification and centrifugation of white blood cells. The pellet resulting from centrifugation, which contains intact white blood cells and associated bacteria, is isolated by decanting the supernatant. The supernatant may contain digested or dead white blood cells and bacteria, excess DTT and DNAse, and residual glycoproteins and DNA following the digestive liquification of the mucoid secretion specimen. At this point, the bacteria are then separated from the intact white blood cells by, for example, lysing the white blood cells. Although a number of methods for lysing cells are known to the art, it is most advantageous to the practice of the present invention to utilize a lysing reagent which is capable of lysing the white blood cells and releasing associated bacteria while at the same time preserving the released bacteria as intact cells. In addition, it is most advantageous to employ a lysing reagent which will not inhibit the activity of at least one DNAse, which DNAse may subsequently be added to the lysed concentrated specimen to digest DNA material released from the white blood cells (or other lysed cells, if such exist).

In the case of a selected bacterial species which is to be-assayed by culture techniques, stain techniques or nucleic acid hybridization techniques, it may be essential to retain the selected bacterial species in cellularly intact form after lysing the white blood cells. Culture techniques, for example, will require viable cells for growth later, while stain techniques will typically require at least cellularly intact bacteria. Although the bacterial assaying step in a nucleic acid hybridization assay will involve lysing of the selected bacterial species, it is nevertheless advantageous to retain the bacteria in a cellularly intact state prior to the final hybridization assay step because premature lysing will expose target RNA or DNA within the bacteria to RNAses and DNAses which may be present in the concentrated specimens. Such nucleases may, for example, derive from lysed white blood cells, from other cells that are lysed within the pellet, or from residual sputum in the concentrated specimen after centrifugation and decanting of supernatant. Furthermore, additional DNAse is preferably added to the concentrated specimens of lysed white blood cells in order to digest DNA released from these cells or other lysed organisms, which DNAse could attack the DNA of the bacterial species selected for assaying if such species is not cellularly intact after lysing of the concentrated specimen of pelleted white blood cells. For all of these reasons, it is preferable to lyse the white blood cells in a manner which leaves cellularly intact the bacterial species selected for assaying.

In the case of mycobacteria, it has been discovered that the lysing reagent sodium deoxycholate is capable of lysing white blood cells associated with the mycobacteria in the concentrated specimen while leaving the mycobacteria cellularly intact against destruction of mycobacterial RNA by RNAses or other components present in the concentrated specimen. It is believed that the mycobacteria are also cellularly intact to sodium deoxycholate to the extent that they remain culture-viable after lysing of the white blood cells with this lysing reagent. Other bacteria, such as enteric bile-resistant pathogens including *Salmonella* and *Shigella,* are also examples of bacterial species that would remain cellularly intact upon lysing of associated white blood cells with sodium deoxycholate.

Other salts of deoxycholate may also be suitable for achieving the selective lysing, as may other lysing reagents. It is considered that any lysing reagent suitable for performing the selective lysing described herein, i.e., lysing of concentrated white blood cells in a manner which releases in a cellularly intact form the selected bacterial species of interest, is within the scope of the claimed invention. As used herein, a bacterium is "cellularly intact" with respect to a given assay methodology if the bacterium is retained in a physical form which renders it capable of being assayed according to that methodology. For example, a culture assay will generally require that the bacteria selected for assaying be cellularly intact to the extent of culture viability, while a nucleic acid hybridization assay will generally require that the bacteria be cellularly intact to the extent that target RNA or DNA within the bacterium is preserved from attack by, for example, residual RNAses or DNAses in the specimen. Other definitions of "cellularly intact" may be pertinent to other assay methodologies. In addition, a white blood cell may be considered to be cellularly intact following liquification and concentration steps described above if the cell is capable of retaining a useful level of association with the target bacteria through the concentration step.

Upon lysing of the concentrated specimen of pelleted intact white blood cells, released intracellular components including DNA will typically render the concentrated specimen into a form too viscous for convenient processing in subsequent assay steps. It is therefore useful to add to the lysed white blood cell concentrated specimen a DNAse or other enzyme capable of digesting nucleic acid material released from the white blood cells or other lysed cells in the concentrated specimen. Therefore, the lysing reagent used to lyse the white blood cells should be one which does not inhibit the activity of at least one DNAse or other enzyme suitable for this post-lysing digestion step. Again, sodium deoxycholate is such a suitable lysing reagent. In contrast, the lysing reagent sodium dodecyl sulfate is believed to inactivate most DNAses and RNAses and is an example of a reagent which is preferably not used in lysing the concentrated specimen of white blood cells if subsequent digestion using a nuclease is contemplated.

The post-lysing DNA digestion step of the present invention may be practiced using DNAse I purified from bovine pancreas to yield a liquified and lysed concentrated specimen. This DNAse is the same as that used in the initial liquification of the starting mucoid secretion specimen, and is preferred in the practice of the present invention. Other DNAses may also be utilized and are within the scope of the invention. As noted above, such a digestion agent should be stable to the lysing reagent used to lyse the concentrated specimen of white blood cells. To the extent that it may be advantageous in later processing steps to inactivate the DNAse or other post-lysing digesting agent, as for example in a nucleic acid hybridization assay where probes composed of complementary DNA are to be added, the digestion reagent should be chosen with this fact in mind. DNAse I from bovine pancreas satisfies these requirements.

The lysing of the concentrated specimen containing pelleted intact white blood cells associated with the bacterial species of interest (if such are present in the specimen) is carried out after decanting the supernatant. An appropriate amount of the lysing reagent, which in the case of sodium deoxycholate (16% in water) is about 2 drops (about 60 microliters) for a starting sputum sample of 1 ml, is added to the white blood cell pellet. The pellet is then resuspended using a vortex mixer and incubated for 5 minutes at room temperature.

Following the lysing step, a DNA digestion agent such as a DNAse is added to the concentrated specimen. In the case of a solution containing 7446 Kunitz units/ml of bovine pancreas DNAse I, one drop (about 50 microliters) contains sufficient enzyme to digest and liquify adequately the DNA released from the white blood cells during the lysing step. The digestion mixture is incubated for about 5 minutes at about 20°-25° C., and yields a concentrated specimen that is sufficiently liquified for further assay steps. If the concentrated specimen, now lysed and digested, is not to be tested immediately for presence of a selected bacterial species, it may in some cases, as for example mycobacteria, be stored at about 2°-8° C. for 24 hours.

Bacteria of the Mycobacterium genus are relatively resistant to destruction of their cellular integrity in part because of the high content of waxy lipid materials in their cell walls. Such bacteria remain cellularly intact for the purposes of nucleic acid hybridization assay techniques to such lysing agents as sodium deoxycholate and sodium dodecyl sulfate. Other bacterial species which are stable to a lysing reagent capable of lysing white blood cells in the centrifugal concentrated specimen may also be treated according to the concentration, lysing and digestion steps described above. As noted above, enteric bile-resistant pathogens may fall in this category. In other cases, however, bacterial species selected for assaying may not remain sufficiently cellularly intact through, for example, the white blood cell lysing step. In such a case, the techniques of the present invention may still be employed advantageously subject to certain modifications.

First, the technique wherein the selected bacterial species to be assayed is concentrated from a sputum sample by isolation of white blood cells associated to the bacteria is a general technique applicable to a wide range of bacterial species. This technique may be utilized as an initial concentrating step regardless of, for example, problems of cellular integrity that may be encountered in subsequent processing steps.

In the case of a nucleic acid hybridization assay, it is desirable to avoid exposure of the nucleic acid content of the bacterial species to be assayed to materials, such as DNAses or RNAses, that may degrade the nucleic acids. If the bacterial species of interest cannot be preserved in a cellularly intact state upon lysing the white blood cells, it may be desirable to proceed directly to a lysing step which simultaneously inactivates any DNAses or RNAses which may be present in the lysed concentrated specimen. For example, the pelleted white blood cells may be lysed with sodium dodecyl sulfate, which acts to inhibit or denature DNAses and RNAses, followed by a sonication step which can cleave released nucleic acids (primarily DNA) and render the lysed concentrated specimen less viscous. Alternately, a lysing reagent such as sodium deoxycholate, which generally does not inactivate DNAses or RNAses, may be used in conjunction with an RNAse inhibitor and an added DNAse. This combination will digest DNA released from the lysed white blood cells and bacteria, thus rendering the concentrated specimen less viscous, and will simultaneously prevent degradation of bacterial RNA molecules that are to be used as hybridization targets in the nucleic acid hybridization assay. Of course, the added DNAse would have to be inactivated prior to adding any DNA hybridization probe to the specimen or, alternatively, an RNA probe could be employed.

The selected bacterial species may be assayed following concentration of the white blood cells in the concentrated specimen. Preferably, the assaying step would follow lysing and digestion as described above. If the selected bacterial species is to be cultured, the concentrated specimen may be treated so as to kill undesired species while preserving the selected species. In the case of mycobacteria, which are relatively hardy, this step may be achieved by treating the concentrated specimen (which has been lysed and digested) with dilute sodium hydroxide. Alternately, it appears that treatment with sodium dodecyl sulfate will selectively kill many bacterial species other than mycobacteria. Another method for selectively culturing the selected bacterial species is to use a culture medium which inhibits growth of all or most microorganisms other than the bacterial strains of interest.

A preferred method of assaying for the presence of the selected bacterial species involves nucleic acid hybridization techniques. A quantitative sample (100 ul, for example) of the lysed, digested concentrated specimen prepared as described above and containing, for example, cellularly intact mycobacteria is transferred to a container for lysing of the bacteria. Lysis of the bacteria should not be performed before inactivation of DNAses and RNAses in the specimen which may interfere with the nucleic acid hybridization procedure. Sodium dodecyl sulfate may be used as such an inactivating agent, and in addition acts to solubilize proteins and other cell components. A glass lysing tube containing glass beads and a lysing reagent such as sodium dodecyl sulfate, the use of which is disclosed in pending U.S. patent application Ser. No. 841,860, filed Mar. 20, 1986 and now abandoned, is particularly suited for this bacterial lysing step. The lysing tubes are capped, placed in a water bath sonicator (50°-70° C.) and sonicated for about 15 minutes. (In order to insure optimal energy transfer, the water in the water bath sonicator is preferably degassed prior to this operation by sonicating for about 15 minutes.)

Following sonication, the lysed concentrated bacterial sample may be subjected to nucleic acid hybridization assay as disclosed, for example, is pending U.S. patent application Ser. No. 816,711, filed Jan. 7, 1986 and now abandoned. The probe reaction mixture may contain a detergent-like reagent such as diisobutylsulfosuccinate, which acts to speed up the hybridization process and inhibit any activity of residual DNAse.

EXAMPLES

Example 1: Lysis of White Cells with Sodium Deoxycholate; Elimination of Viscosity with DNAse I Sputum (0.25 ml) was mixed with a solution of dithiothreitol in phosphate buffer (1 M dithiothreitol, 0.1 M sodium phosphate (pH 7.5)) using a vortex mixer. A solution of 30% deoxychoate (0.5 ml) was added, which caused the specimen to immediately become very viscous due to release of DNA from leukocytes. Ten microliters deoxyribonuclease I (5 mg/ml) were added, and the specimen was again mixed. The viscosity disappeared on standing a few moments at room temperature.

The experiment indicated that DNA could contribute to viscosity in sputum specimens and that DNAse I could act to degrade the DNA and reduce sputum viscosity in the presence of 5% sodium desoxycholate. The experiment also indicated that some sputum specimens do not have sufficiently high levels of endogenous DNAse to efficiently degrade DNA that is contributing to viscosity.

Example 2 Lysis of White Cells with Sodium Deoxycholate; Elimination of Viscosity by Endogenous DNAse Activity One-half ml purulent sputum containing greater than 50 leukocytes per 100x smear on microscopic examination was mixed with 0.5 ml 0.001 M dithiothreitol in 0.01 sodium phosphate buffer, pH 7.5. The sample was mixed on a vortex mixer for a few seconds and allowed to stand at room temperature for 15 minutes during which time it had liquified. A 50 microliter portion was transferred to a test tube and mixed with 2 volumes 10% sodium deoxycholate resulting in an immediate increase in viscosity. The viscosity then disappeared over the subsequent 10–20 seconds.

The experiment indicated that exposure to dithiothreitol at low concentrations did not lyse white cells or release their DNA in a sputum specimen under the conditions used. Addition of sodium desoxycholate lysed the cells and released their DNA which made the solution viscous. The viscosity decreased spontaneously in this specimen, and this was attributed to the action of endogenous DNAses.

Example 3: Liquification of Mucoid Sputum Specimens with Dithiothreitol and DNAse I Twelve sputum specimens of all types including bloody and mucopurulent were mixed with an equal volume of solubilizing reagent containing 1M dithiothreitol, 0.1 M Tris-HCl (pH 8.0), 0.25% DNAse I.

All sputa liquified promptly and completely.

Example 4: Liquification of sputum Specimens with Dithiothreitol and DNAse I with Added Magnesium A pooled sputum sample (from 3 acid-fast smear positive sputum specimens) was mixed with an equal volume 1 M dithiothreitol, 0.1 M Tris-HCl (pH 8.0). Fifty microliters of 0.1 M $MgCl_2$ were added along with 10 $\mu$ 1 DNAse I (20 mg/ml; 1400 units/mg; in 0.15 M NaCl, 50 mM $CaCl_2$.

The sputum specimen liquified well. The addition of $MgCl_2$ appeared to accelerate the liquification process compared with previously treated samples in which the divalent gation (required by DNAse I for activity) was not specifically added.

Example 5: Efficiency of Recovery of Mycobacteria by Centrifugation of White Cells One-half ml of sputum (acid-fast positive) was mixed with an equal volume of 0.1 M Tris-HCl (pH 8.0), 1 M dithiothreitol by vortexing. The liquified sputum was centrifuged for 3 minutes in a clinical centrifuge. The supernatant was retained and set aside. The pellet was washed once with 5 ml. 0.15 M NaCl. The samples were then assayed for mycobacterial RNA by hybridization with an $I^{125}$-labelled DNA probe.

Kinetics of hybridization indicated that there were at least $1.6 \times 10^7$ mycobacteria per 0.5 ml sputum in the cell associated fraction. No mycobacteria were detected in the supernatant fraction, and the maximum number that could have been present without detection was calculated to be about $2 \times 10^6$ per ml. Addition of mycobacterial RNA to the supernatant fraction followed by hybridization assay indicated that the negative result on the supernatant was not due to components that inhibited the hybridization assay. It was concluded that mycobacteria can be efficiently pelleted from a liquified sputum specimen at relatively low centrifugal forces.

Example 6: Repeat of Assays Using Protocol of Example 5 and Four Other Acid-Fast Positive Sputum Specimens The experimental protocol given in example 5 was repeated on four additional sputum specimens with the following results:

Specimen 1: The cell pellet contained about $6 \times 10^6$ mycobacteria total; the supernatant contained a maximum of $3 \times 10^5$ mycobacteria total.

Specimen 2: The cell pellet contained about $4 \times 10^6$ mycobacteria total; the supernatant contained a maximum of $1 \times 10^5$ mycobacteria total.

Specimen 3: The cell pellet contained about $1 \times 10^7$ mycobacteria total; the supernatant contained a maximum of $1 \times 10^5$ mycobacteria total.

Specimen 4: The cell pellet contained about $3 \times 10^6$ mycobacteria total; the supernatant contained a maximum of $2 \times 10^5$ mycobacteria total.

The experiments confirmed that mycobacteria can be efficiently recovered in the white cell fraction of a sputum specimen.

I claim:

1. A method of liquifying a mucoid secretion specimen, comprising the steps of:
   (a) contacting said specimen with a disulfide bond reducing agent so as to cleave disulfide bonds in proteinaceous molecules in said specimen; and
   (b) contacting said specimen with a DNA digestion agent so as to cleave phosphodiester bonds in DNA molecules in said specimen, wherein said reducing agent and said DNA digestion agent are provided as separate molecular species, such that said liquifying of said specimen is greater than when each said reducing agent and said DNA digestion agent is used separately, wherein said reducing agent and said DNA digestion agent are provided as separate molecular species, such that said liquifying of said specimen is greater than when each said reducing agent and said DNA digestion agent is used separately.

2. A method of liquifying a mucoid secretion specimen comprising the steps of firstly contacting said specimen with a disulfide bond reducing agent so as to cleave disulfide bonds in proteinaceous molecules in said specimen; and secondly contacting said specimen with a DNA digestion agent so as to cleave phosphodiester bonds in DNA molecules in said specimen.

3. A method of liquifying a mucoid secretion specimen comprising the steps of firstly contacting said specimen with a DNA digestion agent so as to cleave phosphodiester bonds in DNA molecules in said specimen; and secondly contacting said specimen with a disulfide bond reducing agent so as to cleave disulfide bonds in proteinaceous molecules in said specimen.

4. A method of liquifying a mucoid secretion specimen comprising the steps of contacting said specimen with a disulfide bond reducing agent except N-acetyl cysteine so as to cleave disulfide bonds in proteinaceous molecules in said specimen, and contracting said specimen with a DNA digestion agent so as to cleave phosphodiester bonds in DNA molecules in said specimen, wherein said reducing agent and DNA digestion agent are provided as separate molecular species.

5. A method of liquifying a mucoid secretion specimen except a mucopurulent specimen, comprising the steps of contacting said mucoid secretion specimen except a mucopurulent specimen with a disulfide bond reducing agent so as to cleave disulfide bonds in proteinaceous molecules in said specimen and contacting said specimen with a DNA digestion agent so as to cleave phosphodiester bonds in DNA molecules in said specimen, so that liquification of said specimen is greater than when each agent is used separately.

6. A method of liquifying a mucoid secretion specimen except a mucopurulent specimen, comprising the steps of firstly contacting said specimen except a mucopurulent specimen with a DNA digestion agent so as to cleave phosphodiester bonds in DNA molecules in said specimen, and secondly contacting said mucoid secretion specimen except a mucopurulent specimen with a disulfide bond reducing agent so as to cleave disulfide bonds in proteinaceous molecules in said specimen.

7. The method of claims 1, 2, 3, 4 or 5 wherein said disulfide bond reducing agent is dithiothreitol.

8. The method of claims 1, 2, 3, 4, 5, or 6 wherein said DNA digestion agent is deoxyribonuclease.

9. The method of claim 8 wherein said deoxyribonuclease is deoxyribonuclease I.

10. The method of claim 9 wherein said deoxyribonuclease I is purified from bovine pancreas.

11. The method of claims 1, 2, 3, 4 or 5 wherein the DNA digestion agent contacts the specimen in the presence of a bivalent ion selected from the group consisting of $Ca^{++}$ and $Mg^{++}$.

12. The method of claim 11 wherein the DNA digestion agent is provided in a $Ca^{++}$ solution.

13. The method of claim 11 wherein said DNA digestion agent is deoxyribonuclease I.

14. The method of claim 13 wherein said deoxyribonuclease I is purified from bovine pancreas.

15. A method of liquifying a mucoid secretion specimen except a mucopurulent specimen including the step of contacting said mucoid secretion specimen except a mucopurulent specimen with a mixture comprising a disulfide bond reducing agent and a deoxyribonuclease provided as separate molecular species, so that liquification of said specimen is greater than when each agent is used separately.

16. A method of liquifying a mucoid specimen including the step of contacting said mucoid secretion specimen with a mixture comprising a disulfide bond reducing agent except N-acetyl cysteine and a deoxyribonuclease, wherein said reducing agent and deoxyribonuclease are provided as separate molecular species.

17. The method of claims 6, 15 or 16, wherein said specimen is a sputum specimen.

18. The method of claim 17, wherein the sputum specimen is contacted with the disulfide bond reducing agent dithiothreitol and the deoxyribonuclease deoxyribonuclease I.

19. The method of claims 4, 15 or 16 wherein the deoxyribonuclease contacts the specimen in the presence of a bivalent ion selected from the group consisting of $Ca^{++}$ and $Mg^{++}$.

20. The method of claim 19 wherein the deoxyribonuclease is provided in a $Ca^{++}$ solution.

21. The method of claims 15 or 16 wherein said deoxyribonuclease is deoxyribonuclease I.

22. A method of liquifying a mucoid secretion specimen, comprising contacting said specimen with a digestion mixture comprising a DNA digestion agent capable of cleaving phosphodiester bonds in DNA molecules in said specimen and a disulfide bond reducing agent, wherein Said reducing agent and DNA digestion agent are provided as separate molecular species and such that the combined effect of the DNA digestion agent and the disulfide bond reducing agent is a greater reduction of specimen viscosity than When the agents are used separately.

23. The method of claim 22, wherein said digestion mixture comprises dithiothreitol as the disulfide bond reducing agent.

24. The method of claim 22, where said DNA digestion agent is a deoxyibonuclease.

25. The method of claim 24 wherein said deoxyribonuclease is deoxyribonuclease I.

26. The method of claim 25 wherein said deoxyribonuclease I is purified from bovine pancreas.

27. The method of claim 22, wherein the DNA digestion agent contacts the specimen in the presence of a bivalent ion selected from the group consisting of $Ca^{++}$ and $Mg^{++}$.

28. The method of claim 27 wherein the DNA digestion agent is provided in a $Ca^{++}$ solution.

29. The method of claim 27 wherein said DNA digestion agent is deoxyribonuclease I.

30. The method of claim 29 wherein said deoxyribonuclease I is purified from bovine pancreas.

31. A kit for assaying a mucoid secretion specimen for the presence of a selected bacterial species, including in a first container a composition comprising a disulfide bond reducing agent and in a second container a composition comprising a DNA digestion agent for liquifying said specimen; and means for determining the presence of said bacterial species.

32. The kit of claim 31, wherein said means for determining the presence of said selected biological species includes means capable of detecting a mycobacterium or an enteric bile-resistant pathogen.

33. The kit of claim 31 further including a container comprising a cell lysing agent.

34. The kit of claim 33 wherein said DNA digestion agent is selected so as to retain activity in the presence of said cell lysing agent.

35. The kit of claim 34 wherein said cell lysing agent is a deoxycholate salt.

36. The kit of claim 33 wherein said cell lysing agent is a deoxycholate salt.

37. A kit for assaying a mucoid secretion specimen for the presence of a selected bacterial species, including in a first container a composition comprising a disulfide bond reducing agent and in a second container a composition comprising a deoxyribonuclease for liquifying said specimen; and means for determining the presence of said bacterial species.

38. The kit of claim 37, wherein said means for determining the presence of said selected bacterial species includes means capable of detecting a mycobacterium or an enteric bile-resistant pathogen.

39. The kit of claim 37, wherein the deoxyribonuclease provided in the kit is in a solution containing a source of a bivalent ion selected from the group consisting of $Ca^{++}$ and $Mg^{++}$.

40. The kit of claim 39, wherein the deoxyribonuclease provided in the kit is in a solution containing both the bivalent ions $Ca^{++}$ and $Mg^{++}$.

41. The kit of claim 37 wherein said deoxyribonuclease is deoxyribonuclease I.

42. The kit of claim 41 wherein said deoxyribonuclease I is purified from bovine pancreas.

43. A kit for assaying a sputum specimen for the presence of a selected bacterial species, including a in first container a composition comprising dithiothreitol and in a second container a composition comprising a DNA digestion agent for liquifying said specimen; and means for determining the presence of said bacterial species.

44. The kit of claim 43, wherein said means for determining the presence of said selected bacterial species includes means capable of detecting a mycobacterium or an enteric bile-resistant pathogen.

* * * * *